United States Patent
Zhuravlev et al.

(10) Patent No.: US 9,856,182 B2
(45) Date of Patent: Jan. 2, 2018

(54) RADIOFLUORINATION METHOD

(71) Applicant: TECHNICAL UNIVERSITY OF DENMARK, Lyngby (DK)

(72) Inventors: Fedor Zhuravlev, Roskilde (DK); Bente Mathiessen, Roskilde (DK)

(73) Assignee: TECHNICAL UNIVERSITY OF DENMARK, Kgs. Lyngby (DK)

( * ) Notice: Subject to any disclaimer, the term of this patent is extended or adjusted under 35 U.S.C. 154(b) by 259 days.

(21) Appl. No.: 14/417,749

(22) PCT Filed: Jul. 30, 2013

(86) PCT No.: PCT/EP2013/066025
§ 371 (c)(1),
(2) Date: Jan. 27, 2015

(87) PCT Pub. No.: WO2014/020035
PCT Pub. Date: Feb. 6, 2014

(65) Prior Publication Data
US 2015/0299066 A1    Oct. 22, 2015

(30) Foreign Application Priority Data

Jul. 30, 2012 (DK) .......................... PA 2012 00482
May 24, 2013 (DK) .......................... PA 2013 00319

(51) Int. Cl.
| | | |
|---|---|---|
| *A61K 51/00* | (2006.01) | |
| *A61M 36/14* | (2006.01) | |
| *C07B 59/00* | (2006.01) | |
| *A61K 51/06* | (2006.01) | |
| *A61K 51/12* | (2006.01) | |
| *B01J 19/24* | (2006.01) | |
| *B01D 15/36* | (2006.01) | |

(52) U.S. Cl.
CPC .......... *C07B 59/004* (2013.01); *A61K 51/065* (2013.01); *A61K 51/1244* (2013.01); *B01J 19/24* (2013.01); *C07B 59/00* (2013.01); *B01D 15/36* (2013.01); *B01J 2219/24* (2013.01); *C07B 2200/11* (2013.01)

(58) Field of Classification Search
CPC .. C07B 59/004; A61K 51/065; A61K 51/1244
USPC ....................................................... 424/1.89
See application file for complete search history.

(56) References Cited

U.S. PATENT DOCUMENTS

| | | | |
|---|---|---|---|
| 6,190,637 B1 | 2/2001 | Ino et al. | |
| 2006/0083677 A1 | 4/2006 | Brady et al. | |
| 2008/0305042 A1* | 12/2008 | Gacek et al. | 424/1.89 |
| 2010/0196254 A1* | 8/2010 | Lemaire et al. | 423/501 |
| 2011/0006011 A1 | 1/2011 | Aerts et al. | |

FOREIGN PATENT DOCUMENTS

| | | |
|---|---|---|
| KR | 1020080072233 | 8/2008 |
| WO | 2008/128306 | 10/2008 |
| WO | 2009/003251 | 1/2009 |
| WO | 2011/110994 | 9/2011 |

OTHER PUBLICATIONS

Mathiessen et al. Chem. Eur. J. 2011, 17, 7796-7805.*
Xu et al. Bioorg. Med. Chem. Lett. 1998, 8, 1089-1092.*
International Search Report and Written Opinion dated Oct. 17, 2013 in corresponding International Patent Application No. PCT/EP2013/066025.
Denmark Office Action and Search Report dated Feb. 21, 2013 in corresponding Denmark Patent Application No. PA 2012 00482.
Steven A. Toorongian et al., "Routine Production of 2-Deoxy-2-[$^{18}$F]fluoro-D-glucose by Direct Nucleophilic Exchange on a Quaternary 4-Aminopyridinium Resin," Nucl. Med. Biol., vol. 17, No. 3, pp. 273-279 (1990).
Bente Mathiessen et al., "Homogeneous Nucleophilic Radiofluorination and Fluorination with Phosphazene Hydrofluorides," Chem. Eur. J., vol. 17, pp. 7796-7805 (2011).
David J. Schlyer et al., "Separation of [$^{18}$F]fluoride from [$^{18}$O]water using anion exchange resin" International Journal of Radiation Applications and Instrumentation. Part A. Applied Radiation and Isotopes, vol. 41, No. 6, pp. 531-533 (1990).

* cited by examiner

*Primary Examiner* — Michael G Hartley
*Assistant Examiner* — Sean R Donohue
(74) *Attorney, Agent, or Firm* — Pillsbury Winthrop Shaw Pittman LLP (57) ABSTRACT

A method of conducting radiofluorination of a substrate, includes: (a) contacting an aqueous solution of [$^{18}$F] fluoride with a polymer supported phosphazene base for sufficient time for trapping of [$^{18}$F] fluoride on the polymer supported phosphazene base; and (b) contacting a solution of the substrate with the polymer supported phosphazene base having [$^{18}$F] fluoride trapped thereon obtained in step (a) for sufficient time for a radiofluorination reaction to take place.

16 Claims, 3 Drawing Sheets

RADIOFLUORINATION METHOD

CROSS REFERENCE TO RELATED APPLICATIONS

This application is the National Phase entry of PCT/EP2013/066025, which claims priority to Denmark Patent Application No. PA 2013 00319, filed May 24, 2013 and Denmark Patent Application No. PA 2012 00482, filed Jul. 30, 2012. The content of these applications is incorporated herein by reference in their entirety.

The present invention relates to a method of radiofluorination, in particular that can be used for dose-on-demand and/or bedside production of $^{18}$F PET radiotracers.

Positron emission tomography (PET) is an imaging method used to obtain quantitative molecular and biochemical information regarding physiological processes in the human body. The most common PET radiotracer in use is $^{18}$F-fluorodeoxyglucose ($^{18}$F-FDG), a radiolabelled glucose molecule. PET imaging with $^{18}$F-FDG allows the visualisation of glucose metabolism and has a broad range of clinical uses. $^{18}$F is the most widely used positron emitter in the clinical environment.

$^{18}$F fluoride is produced by the irradiation of water containing $H_2{}^{18}O$ with protons, resulting in the reaction $^{19}O(p,n)^{18}F$. Only a minor fraction of the $^{18}O$ is converted. For production efficiency and radiochemical purity, it is desirable to use water that is as highly enriched as possible. The $^{18}$F isotope is then separated from the water and processed for reaction to produce a radiochemical agent, as, due to the high free energy of hydration of $^{18}F^-$, this species is nucleophilically inert in aqueous solution. Routinely, the removal of water is achieved by trapping $^{18}F^-$ on an ion exchange resin, eluting the trapped $^{18}F^-$ from the resin using a cryptand ligand and a base (for example Kryptofix 222-$K_2CO_3$) dissolved in organic solvent, and removal of the water by repeated and time consuming azeotropic distillations, which process is unsuitable for miniaturisation.

Improvement of the production of $^{18}F^-$ has been attempted. WO2008/128306 (Voccia et al) describes a method of removing water from the $^{18}F^-$ and providing it in an organic solvent suitable for conducting fluorination reactions, which method is conducted without the need for azeotropic distillation of water. This document teaches the use of a non-ionic solid support modified with a trapping agent which is a metal salt complex of a positively charged base such as a cryptand or polydentate amine ligand, which trapping agent is able to remain bound to the solid support in aqueous solution, but is released from the solid support when exposed to a polar aprotic solvent suitable for radiolabelling. Thus, the $^{18}F^-$ is bound to the solid support as a complex with the trapping agent, and is subsequently eluted in the chosen polar aprotic organic solvent in the form of an $^{18}F^-$-trapping agent complex. An intermediate elution step can eliminate the majority of the water while allowing the $^{18}F^-$ and trapping agent to remain bound to the solid support, if a suitable organic solvent is selected. The eluted $^{18}F^-$-trapping agent complex in solution in the polar aprotic solvent is suitable for conducting radiolabelling.

Similarly, Lemaire et al (Angewandte Chemie Int Ed 2010, 49, 3161-3164) describe the elution of $^{18}F^-$ from a solid support using acetonitrile and a variety of bases such as BEMP, BTMG, $P_2{}^{Et}$ and $P_4{}^{tBu}$, followed by use of the eluted solution in the radiofluorination of a number of precursors of PET radiotracers.

US2011/0006011 (Aerts et al) describes the trapping of $^{18}F^-$ on an anion exchange column, rinsing with organic solvent to remove water, and elution with an organic solution containing a tertiary alcohol and/or a phase transfer agent. The resulting solution can be used for radiolabelling reactions.

KR20080078233 (Yoon et al) describes a method in which $^{18}F^-$ is trapped on a quaternary ammonium salt supported on a polymer support, the $^{18}F^-$ is eluted by a solution comprising a metal ammonium salt in an alcoholic solvent, and subsequently the eluted solution is reacted with an alkyl halide or alkyl sulphonate.

U.S. Pat. No. 6,190,637 (Ino et al) describes a method of isolating $^{18}F^-$ from $H_2{}^{18}O$ by trapping it on a weakly basic anion exchange resin, and subsequently eluting it in the form of a complex with a phase transfer catalyst such as a cryptand. The eluted solution is an aqueous solution, and so the $^{18}F^-$ complex must be dried and redissolved in a suitable organic solvent before a radiolabelling reaction can be carried out.

Schlyer et al (Appl Radiat Isot 1990, 41, 6, 531-533) also describes a method in which $^{18}F^-$ is isolated from $H_2{}^{18}O$ by binding to an anion exchange resin. The trapped $^{18}F^-$ is eluted from the resin using a dilute solution of caesium carbonate or potassium carbonate in water.

US2006/0083677 (Brady et al) describes a method in which a precursor molecule for radiolabelling, in particular a benzothiazole compound, is bound to a solid support, and $^{18}F^-$ is contacted with the solid support and reacts with the precursor molecule by displacing the support to result in a labelled tracer molecule.

WO2011/110994 describes a method of producing a radio tracer by nucleophilic displacement by $^{18}F^-$ of a labelled leaving group, and subsequent removal of unreacted precursor by use of an adsorbent recognising the labelled leaving group.

Toorongian et al (Nucl Med Biol 1990, 17, 3, 273-279) describes the use of $^{18}F^-$ supported on a quaternary 4-(N,N-dialkylamino)-pyridinium functionalised polystyrene anion exchange resin for conducting radiofluorination reactions to produce radiolabelled $^{18}$F-FDG. The $^{18}F^-$ is captured directly by the resin from $H_2{}^{18}O$, acetonitrile is passed through the column to remove water from the resin, and an acetonitrile solution of the precursor compound for the radiofluorination passed through the column while heating in order to conduct the radiofluorination reaction. The resin columns are stated not to be reusable as the resin becomes strongly discoloured during normal reaction conditions, although the mechanism of decomposition of the resin is not known.

Mathiessen et al (Chem Eur J 2011, 17, 7796-7805) describes the formation of phosphazenium hydrofluorides by trapping of gaseous HF, and $H^{18}F$, by phosphazene bases. These phosphazenium hydrofluorides, in particular $P_2{}^{Et}$ and $P_4{}^{tBu}$ hydrofluorides, were used to carry out solution phase fluorination and radiofluorination reactions on alkyl halides and pseudohalides, and optimisation of the conditions for conducting the fluorination reactions was carried out.

It is an aim of the present invention to provide an efficient method of trapping $^{18}F^-$ from aqueous solution and delivering it to a target molecule as a nucleophile.

An aim of certain embodiments of the present invention is to provide such a method for preparation of radiotracers for PET imaging.

An aim of certain embodiments of the present invention is to provide such a method that is suitable for bedside production of radiotracers, or other applications in which miniaturisation of the apparatus is desirable.

An aim of certain embodiments of the present invention is to provide a method in which the apparatus can be re-used.

An aim of certain embodiments of the present invention is to provide apparatus which is stable at room temperature.

An aim of certain embodiments of the present invention is to remove the need for purification steps and/or the use of solution phase complexing agents in the generation and use of $^{18}F^-$.

An aim of the present invention is to provide a method in which $^{18}F^-$ recovery and radiofluorination can take place within the same vessel or column.

An aim of certain embodiments of the present invention is to provide more rapid methods of trapping $^{18}F^-$ and subsequent radiolabelling reactions, in particular to provide rapid on demand synthesis of radiotracers.

An aim of certain embodiments of the present invention is to provide a disposable cartridge that can be used in the production of radiotracers.

Accordingly, in a first aspect, the present invention provides a method of conducting radiofluorination of a substrate, comprising the steps of:

(a) contacting an aqueous solution of [$^{18}F$] fluoride with a polymer supported phosphazene base selected from a phosphazene of the general formula R = alkyl supported on polystyrene ($P_{PS}$-$P_2^R$), and a phosphazene of the formula supported on PEG-coated polystyrene ($P_{PS\text{-}PEG}$-$P_2^{Bz}$) for sufficient time for trapping of the [$^{18}F$] fluoride by the polymer-supported phosphazene base; and (b) contacting a solution of the substrate with the polymer supported phosphazene base having [$^{18}F$] fluoride trapped thereon obtained in step (a) for sufficient time for a radiofluorination reaction to take place.

Preferably, the radiofluorination method further comprises a step of preparing an aqueous solution of $^{18}F^-$ by $^{18}O(p, n)^{18}F$ reaction in a cyclotron using enriched $H_2^{18}O$ water.

Preferably, following step (a) and before step (b), residual water is removed from the polymer supported phosphazene base having [$^{18}F$] fluoride trapped thereon by contacting it with a water-miscible solvent. The removal step may suitably be carried out by flowing the water miscible solvent over the polymer supported phosphazene base having [$^{18}F$] fluoride trapped thereon, or by one or more iterations of immersing the polymer supported base having [$^{18}F$] fluoride trapped thereon in the water miscible solvent and then removing the water miscible solvent. Preferably, the water miscible solvent is selected from acetonitrile, THF, DMF and acetone. Suitably, the polymer supported phosphazene base having [$^{18}F$] fluoride trapped thereon can be further dried by passing a flow of dry gas over it.

Suitably, following step (a) and any drying steps, and prior to step (b), the polymer supported phosphazene base having [$^{18}F$] fluoride trapped thereon can be contacted with organic solvent to allow for swelling of the polymer support. Preferably, the organic solvent is the same as the solvent used to prepare the substrate solution to be used in step (b).

Preferably, the substrate solution is prepared using toluene, acetonitrile, dichloromethane or DMF as solvent.

The substrate used in step (b) is an aliphatic or aromatic compound comprising a leaving group. The leaving group is suitably selected from the group consisting of fluorosulfonates, perfluoroalkysulfonates, alkanesulfonates, arenesulfonates, alkyl, perfluoroalkyl or arene esters, phosphate, sulphate or nitrate esters, alkyl or aryl diazonium salts, ammonium, tetraalkylammonium or pyridinium salts, ethers or thioethers, halogens (other than fluoride), nitro groups and diiodoaryliodonium salts. Preferably, the leaving group is selected from the group consisting of triflate, nosylate, mesylate, tosylate, chloride, bromide, iodide and nitro. Preferably, the compound comprising the leaving group is selected from naphthylethyl compounds, mannose, optionally substituted pyridine compounds and glycols.

Preferably, the polymer supported phosphazene base is contained in a column. Suitably, the column can be re-used in more than one iteration of the method of the invention. Suitably, the column can be sealed and disposed of after a chosen number of iterations of the method of the invention.

Preferably, where the polymer supported phosphazene base is of the formula

R = alkyl supported on polystyrene, R is selected from the group consisting of methyl, ethyl, propyl, butyl, isopropyl, isobutyl, tert-butyl, pentyl, isopentyl, tert-pentyl, tert-octyl, and more preferably is selected from the group consisting of ethyl, tert-butyl and tert-octyl.

Preferably, the polymer supported phosphazene base is selected from $P_{PS}$-$P_2^{tBu}$ and $P_{PS-PEG}$-$P_2^{Bz}$ Preferably, step (b) comprises heating the polymer supported phosphazene base having [$^{18}$F] fluoride trapped thereon in contact with the substrate solution to a temperature of from 50° C. to 120° C.

Preferably, the product of the reaction in step (b) is isolated from the polymer supported phosphazene base. Where the polymer supported phosphazene base is contained in a column, this can be done by passing a suitable organic solvent, such as the solvent in which the substrate was dissolved, through the column.

Preferably, following step (b), a purification step is conducted, in which the product of the reaction between the polymer supported phosphazene base having [$^{18}$F] fluoride trapped thereon and the substrate solution is contacted with a solid phase adsorbent. The solid phase adsorbent may conveniently be provided in a column or cartridge, in a known manner.

Suitably, following step (b), the polymer supported phosphazene base can be cleaned for re-use by contact with an organic solvent, preferably the same solvent as that in which the substrate was dissolved, and optionally also by heating the polymer supported phosphazene base and solvent to a temperature of from 50° C. to 120° C.

Suitably, more than one iteration of the steps (a) and (b), and, if desired, of one or more of the optional steps described above, may be carried out.

In a second aspect, the present invention provides a method of preparation of a radiotracer for administration to a patient, comprising the radiofluorination method according to the first aspect of the invention, followed by a step of formulation of the product of step (b) for administration to the patient. Suitably, the formulation step comprises removal of the solvent from the product of step (b), which product may optionally have been purified as described in the first aspect of the invention, dissolution of the product in saline solution, and filtration of the saline solution through a sterile filter.

In a third aspect, the present invention provides an apparatus for conducting radiofluorination reactions, such as those according to the first aspect of the invention, comprising a polymer supported phosphazene base selected from a phosphazene of the general formula

R = alkyl supported on polystyrene ($P_{PS}$-$P_2^R$), and a phosphazene of the formula supported on PEG-coated polystyrene ($P_{PS-PEG}$-$P_2^{Bz}$) contained in a column.

Preferably, where the polymer supported phosphazene base is of the formula

R = alkyl supported on PEG-coated polystyrene, R is selected from the group consisting of methyl, ethyl, propyl, butyl, isopropyl, isobutyl, tert-butyl, pentyl, isopentyl, tert-pentyl, tert-octyl, and more preferably is selected from the group consisting of ethyl, tert-butyl and tert-octyl.

Preferably, the polymer supported phosphazene base is selected from $P_{PS}\text{-}P_2^{tBu}$ and $P_{PS\text{-}PEG}\text{-}P_2^{Bz}$ Preferably, the apparatus further comprises one or more elements selected from: means, such as tubing, for connection of the column to other apparatus, such as a cyclotron, vessels containing solvents, substrate solutions, aqueous solutions of $^{18}F^-$; means, such as tubing, for connection of the column to a gas line; one or more vessels for supply of solvent, substrate solution, aqueous solution of $^{18}F^-$ to the column, and for the collection of waste from the column; a second column containing solid phase adsorbent for purification of the product of the radiofluorination reaction; sealing means for isolating the column prior to disposal.

Preferably, the column is for use in production of radiotracers, such as those according to the second aspect of the invention.

In a fourth aspect, the present invention provides the use of a column according to the third aspect of the invention in conducting radiofluorination reactions, such as those according to the first aspect of the invention.

Preferably, the use is in the production of radiotracers, such as those according to the second aspect of the invention.

In a fifth aspect, the present invention provides an apparatus for production of a dose of a radiotracer for administration to a patient, which apparatus comprises:
(a) a cyclotron;
(b) a radiosynthesis module, comprising a column according to the third aspect of the invention; and
(c) a formulation module.

Preferably, the apparatus is shielded to prevent exposure of an operator to radiation. Preferably, the apparatus is arranged such that it can be operated remotely.

Preferably, the cyclotron can operate at 7.8 MeV and is able to produce $^{18}F$, $^{13}N$ and $^{11}C$ isotopes. However, any known cyclotron able to produce $^{18}F$ may suitably be used.

Preferably, the radiosynthesis module further comprises one or more of: a heating element, a gas supply, syringe pumps, valve systems for control of the supply of gases and solutions to the column, and a second column containing solid phase adsorbent.

Preferably, the formulation module comprises [apparatus for evaporation of solvent], such as a heating element and a supply of inert gas, provided in order that the solution can be heated under a flow of the inert gas; a vessel containing saline solution, [means for introducing the saline solution to the radiotracer], and a sterile filter.

Suitably, the apparatus further comprises a quality control module, which suitably comprises a radio-HPLC, a gas chromatograph, and a pH meter.

It is envisaged that preferred features described for one aspect of the invention may be combined with any other aspect of the invention.

DETAILED DESCRIPTION

Figure 1:
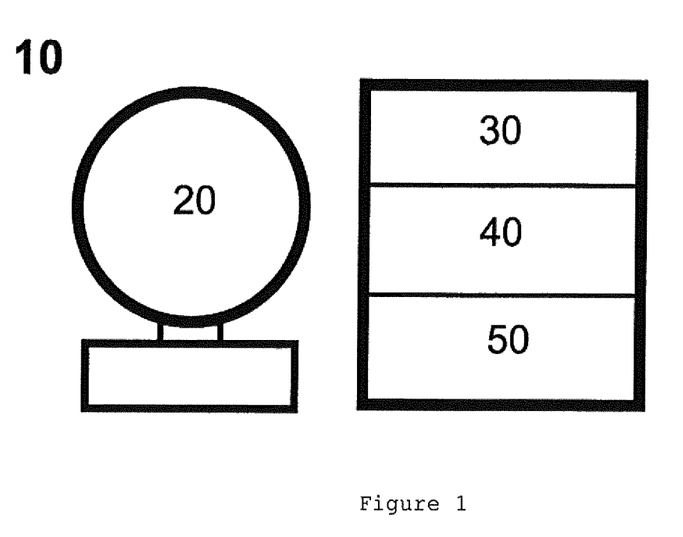
FIG. 1 shows a schematic representation of a dose-on-demand radiofluorination apparatus.

Referring to FIG. 1, the dose-on-demand instrument 10 is a self-shielded, remotely operated instrument consisting of
(1) a compact cyclotron 20 operating at 7.8 MeV and able to produce 18F, 13N, and 11C radioisotopes,
(2) a radiosynthesis module 30, connected to the compact cyclotron and consisting of heating elements, gas line, syringe pumps, and a disposable radiochemical cartridge,
(3) A formulation module 40,
(4) A quality control module 50.

Figure 2:
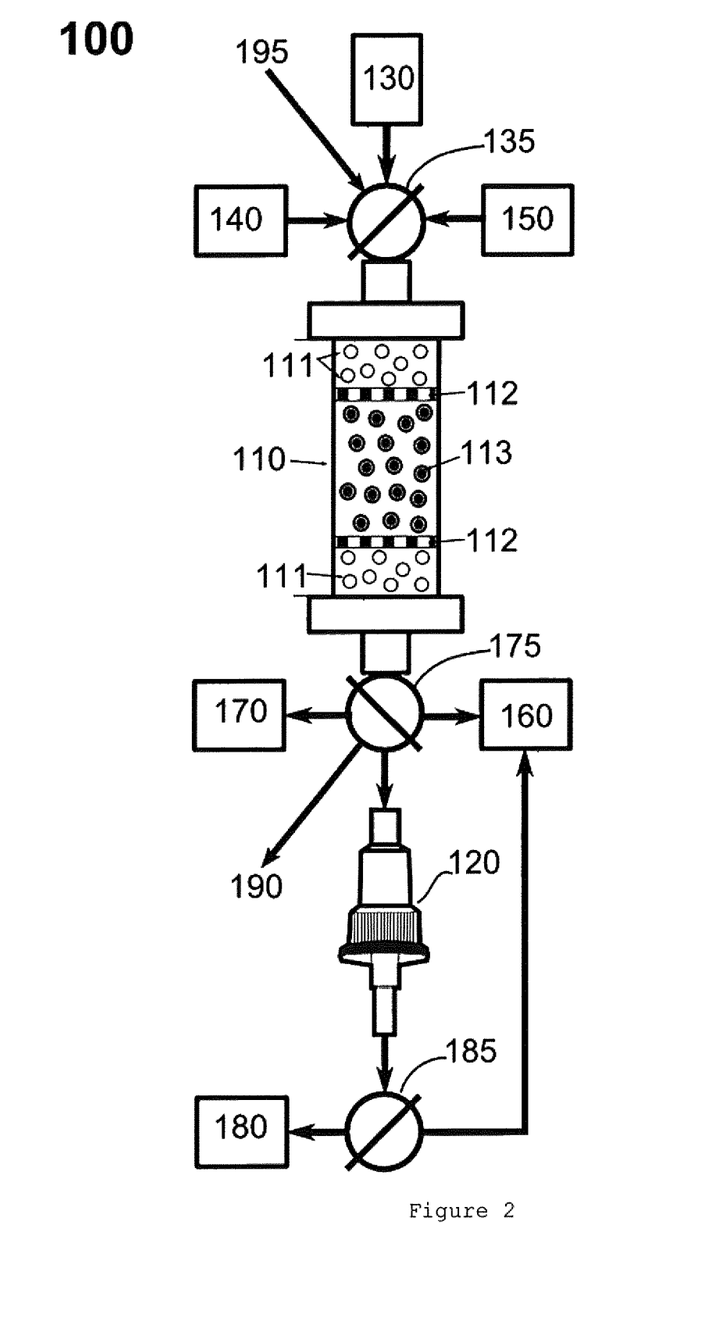
FIG. 2 shows the apparatus for on-column $^{18}F^-$ recovery and radiofluorination.

Referring to FIG. 2, the apparatus (100), ie the radiochemical cartridge included in the radiosynthesis module 30 of the dose-on-demand instrument 10, comprises the following elements: the column (110), which performs [$^{18}F$] fluoride trapping and on-column radiofluorination, an optional solid phase extraction cartridge (120) for product purification, vessels to hold the substrate (130), [$^{18}O$] water (target water) (140), solvents (150), waste (160), waste [$^{18}O$] water (170) and the product (180), and the gas line (190+ 195). These elements are interconnected by tubing (arrows) and valves (135, 175, 185).

The column (110) can be made of glass, such as borosilicate glass, or plastic, such as PTFE. The column is packed with appropriate polymer supported phosphazene base (113). Unreactive fillers, such as glass beads (111) and/or glass wool (112) can be optionally added to minimize the dead volume of the column.

The said polymer supported phosphazene base (113) comprises a phosphazene base residue covalently bound to a solid phase support, which is insoluble in any solvents to be used in the process. Examples of suitable polymer support include, but are not limited to, polymers such as polyethylene, polystyrene, poly(ethylene terephthalate), polycaprolactam, poly(p-phenylene), polybenzimidazole, polyimide, poly(phenylene oxide), polyfluoroethylene, or any co-polymers or polyethylene glycol (PEG) derivatives of these. These polymers may be block grafted, and/or crosslinked with crosslinking agents, such as ethylene glycol diacrylate, N,N'-methylenebisacrylamide, divinylbenzene or any combination of these. The said polymer support may also comprise glass or silicon coated with such a polymer. Furthermore, said polymer support may also be in the form of small discrete particles such as beads, or as a coating on the inner surface of a cartridge or on a microfabricated vessel.

A general structure for phosphazene bases is given below. The phosphazene residue can be optionally substituted with alkyl, aryl, benzyl or PEG groups, and/or any fluorinated derivatives thereof. The $R_1$-$R_{15}$ groups can be a part of the same polymer or can be linked to the same or different polymers.

The polymer supported phosphazene base residue used in the present invention comprises a phosphazene with two or more phosphazene units (n≥0).

The inventors have found that attempting fluoride trapping and subsequent fluorination of a substrate with a number of different polymer and glass supported bases occurs in good yield only with $P_{PS}$-$P_2^{tBu}$ and $P_{PS-PEG}$-$P_2^{Bz}$. Compounds such as $P_{PS}$-$P_2^{Et+}Cl^-$ and $P_{PS}$-$P_2^{Bz}$ are able to trap $^{18}F^-$, but are then unreactive towards the fluorination substrate. Bases such as diisopropylaminomethylbenzene supported on polystyrene, P-BEMP and G-$P_2^{Bz}$ were found to be unreactive towards trapping of $^{18}F^-$ from aqueous solution. These results differ from those that might be expected from the prior art: for example, BEMP is disclosed by Lemaire et al to trap and elute $^{18}F^-$ from aqueous solution; and $P_2^{Et}$ and $P_2^{tBu}$ hydrofluorides are taught to have similar reactivity towards fluorination reactions in solution. It is clear that the solid support has a significant effect on the reactivity of the supported base, as can be seen from the difference in reactivity between glass-supported (G-) $P_2^{Bz}$, polystyrene-supported ($P_{PS}$-) $P_2^{Bz}$ and the same base supported on PEG-coated polystyrene ($P_{PS-PEG}$-$P_2^{Bz}$). These results are not P predictable based on the teachings of the prior art.

It is expected that polymer supported phosphazene bases having a structure closely related to $P_{PS}$-$P_2^{tBu}$ will also be useful in the present invention, as it is taught in Schwesinger et al that phosphazene bases of the following general formula have similar reactivity:

R = alkyl

In use, the cartridge is unsealed and inserted into the radiosynthesis module 30 of the dose on demand apparatus 10. It is then prepared for use by connecting its parts to the valves 135, 175, and 185, hosted by the dose on demand instrument. The connections use standard fittings, Luer locks and flanged PTFE tubing used in modern HPLC systems. The tubing is 1/16" (1.59 mm) in diameter for liquid transfer and 1/8" (3.18 mm) for gas transfer. The vessels 130, 140, 150, 160, 170 and 180 for reagents, solvents, starting materials and products are regular 10-100 mL vials made of borosilicate glass and fitted with rubber septa. These are connected to the valves 135, 175 and 185 via flanged tubing fitted with regular needles. The purification cartridge or cartridges 120 can be chosen from any commercially available solid phase extraction (SPE) cartridges based on silica, alumina, C18 or molecularly imprinted polymers and available from commercial vendors, such as Waters, Supelco, and Polyintell. A solution of substrate is loaded into vessel 130, and solvent into vessel 150. Gas line 195 is connected to a suitable gas supply. The aqueous solution of $^{18}F^-$ is then transferred from the cyclotron 20 in which it has been prepared in a known manner, and is introduced into the appropriate vessel 140. As shown in step 220 of FIG. 3, valves 135 and 175 are then opened to allow the aqueous solution of [$^{18}F$] fluoride to flow to the said column 110, containing phosphazene base bound to polymer support. The aqueous solution of $^{18}F^-$ can be allowed to flow through the column 110 at various flow rates, or alternatively, left on the column for a period of time enough to ensure sufficient absorption of [$^{18}F$] fluoride on to the phosphazene base.

Figure 3:
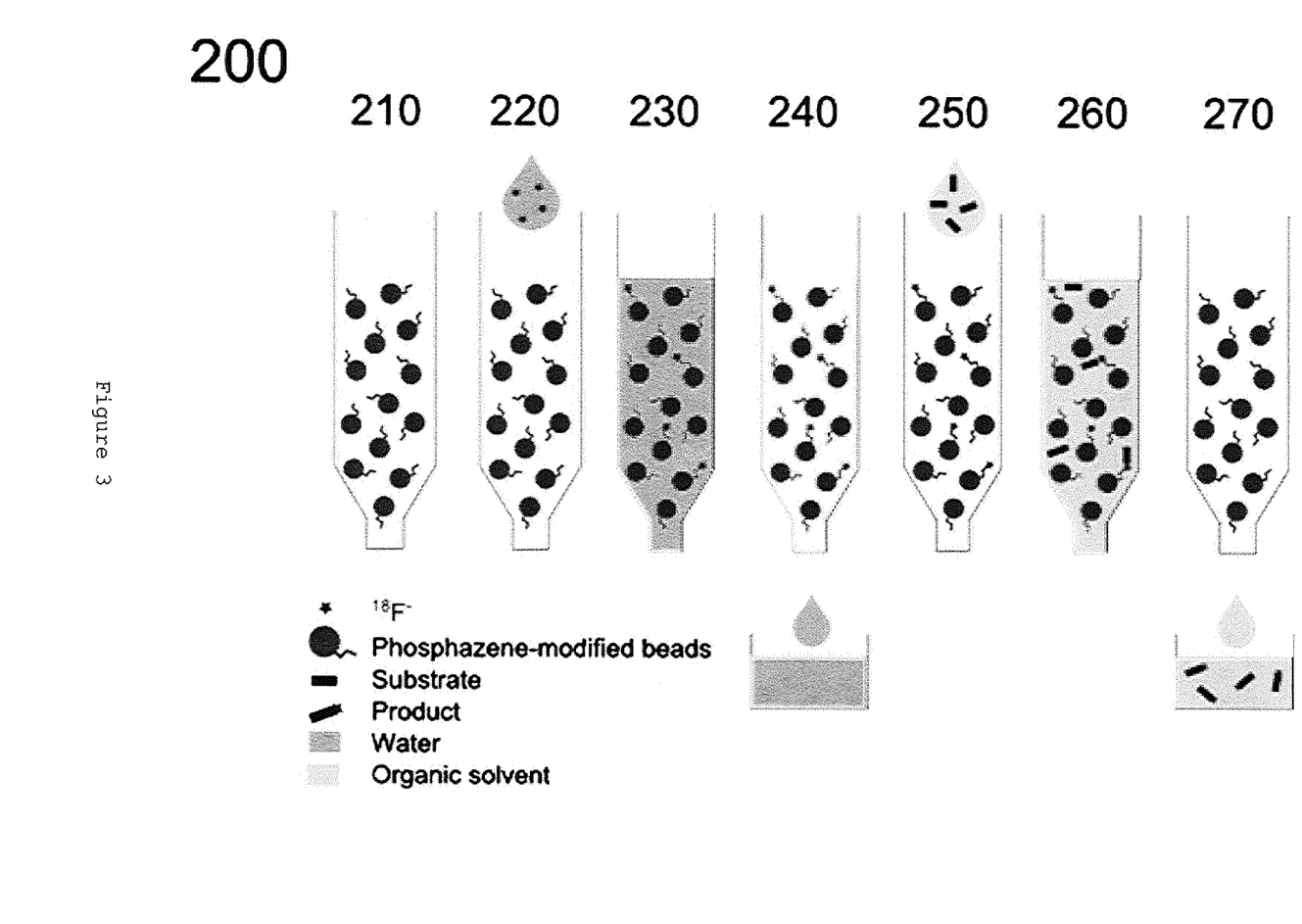
FIG. 3 shows a conceptual representation of on-column $^{18}F^-$ recovery and radiofluorination.

As shown in step 240 of FIG. 3, the residual water can then be removed from the column by a single-time or repeated rinsing of the column with dry organic solvent miscible with water, such as acetonitrile, THF, DMF or acetone, by opening valve 135 such that solvent can flow from vessel 150 and opening valve 175 such that the residual water can pass to waste vessel 170.

Further drying can be achieved by passing a flow of dry gas, such as air, nitrogen, argon or helium through the column. This can be achieved by opening valve 135 to permit gas flow from gas line 195 to the column, and opening valve 175 to permit gas flow from the column to pass to the gas exit line 190.

Once the column has been satisfactorily dried, valve 135 is opened to permit flow of the substrate solution from vessel 130 to the column. This is shown at step 250 of FIG. 3. The solution of substrate is then passed through the column at a suitable flow rate by opening valve 175 to permit the solution to flow from the column 110 towards the product vessel 180, or alternatively, left on the column for a period of time previously determined to be enough to ensure a sufficient degree of substitution of the leaving group in the substrate by the [$^{18}F$] fluoride, by closing valve 175 once the desired quantity of substrate solution has entered column 110. This reaction can be further assisted by heating the column to 50-120° C. The reaction step is shown at step 260 of FIG. 3.

Prior to permitting flow of the substrate the column containing phosphazene base bound to polymer support may be optionally treated with an organic solvent to allow for swelling of the resin. This can be achieved by opening valve 135 so as to permit flow of solvent from vessel 150 to the column, and opening valve 175 to permit solvent leaving the column to pass to waste vessel 160.

A suitably substituted substrate is an aliphatic or aromatic compound comprising a leaving group. This leaving group may comprise, but is not limited to, fluorosulfate, perfluoroalkanesulfonates, such as triflate or nonaflate, alkane sulfonates, such as mesylate or tresylate, arenesulfonates, such as benzenesulfonate, tosylate, brosylate, nosylate, and trinosylate, the derivatives of alkyl and perfluoroalkyl esters, such as acetate and trifluoroacetate, the derivatives of arene esters, such as benzoate and p-nitrobenzoate, the derivatives of phosphate, sulphate and nitrate esters, alkyl or aryldiazonium salts, ammonium, tetralkylammonium and pyridinium salts, the derivatives of ethers and thioethers, such as phenolates, nitrophenolates, and thiophenolates, diiodoaryliodonium salts, nitro groups and halogens other than fluoride.

The substrate can be dissolved in a suitable organic solvent, such as toluene, acetonitrile, dichloromethane, or DMF before applying to the column.

After the reaction is taken to the desired degree of conversion, the reaction mixture is pushed from the column with a new portion of solvent, as shown in step 270 of FIG. 3. This is achieved by opening the valve 135 to allow solvent to flow from vessel 150 to column 110, and opening valve 175 to allow the solution on the column to flow towards solid phase purification cartridge 120. The cartridge 120 contains a solid phase suitable to adsorb any side products, starting material and other contaminants from the solution obtained from the column that must be removed prior to administration of the radiofluorinated product to a patient. The radiofluorinated product is eluted from cartridge 120 by continuing to pass solvent from vessel 150 through the system, and valve 185 is opened to permit flow of the product solution to product vessel 180. When contaminants are eluted from the cartridge 120, valve 185 is opened to permit flow of the eluted solution to waste vessel 160.

The purified product is then transferred to the formulation module where the organic solvent is evaporated, suitably by heating the solution and flowing an inert gas over it, and the product is dissolved in a saline solution and filtered through a sterile filter. The saline solution of the product is then passed to the quality control module, where it is analysed to determine that it is in a suitable condition to be administered to a patient, by analysis by radio-HPLC, gas chromatography and a pH meter.

The column can be optionally cleaned in between the doses by opening the valves 150 and 175 and allowing the solvent from vial 150 to flow towards waste vessel 160. The column 110 can be heated to 50-120° C. to assist desorption of impurities from the column. The column is then dried with a stream of gas.

Once the apparatus has been used for the preparation of the desired number of doses of radiotracer, the disposable cartridge, consisting of the column and all the vessels and tubing described above are sealed and disconnected from the dose-on-demand apparatus 10 and are disposed of in a suitable manner.

EXAMPLES

Materials and Equipment

All solvents and reagents were purchased from Aldrich. Unless otherwise noted, diethyl ether, THF and toluene were distilled from sodium benzophenone; acetonitrile, dichloromethane, DMF, HMPA, tetramethylurea and mesitylene were dried over activated molecular sieves (220° C., 0.1 mbar, 4 hours) for at least 48 hours prior to use; hexane was used as received. Phosphazene base $P_2^{Et}$, phosphazene base $P_2$-$^tBu$ on polystyrene, polymer bound BEMP and diisopropylaminomethyl benzene supported on polystyrene were obtained from Aldrich.

The columns were prepared using PTFE tubing (OD 0.25 inch (0.64 cm)) purchased from Aldrich. The glass beads (212-300 µm), used as neutral filler, were also purchased from Aldrich. All radiochemical yields were decay corrected. $^{18}F$ aqueous solutions were prepared by a $^{18}O(p,n)$ $^{18}F$ reaction in a GE PETtrace cyclotron using a 2.5 ml target of 95-98% enriched $^{18}O$ water irradiated by a 16.5 MeV proton beam at 55 µA for 60-90 min. RadioTLC was performed using Raytest MiniGita TLC-scanner.

Column Preparation

Polymer-$P_2^tBu$ (100 mg, $P_2^tBu$ loading 1.6 mmol/g resin) was mixed with glass beads (1200 mg) and packed in a PTFE tube.

Example 1: $^{18}F^-$ Trapping and Radiofluorination of an Aliphatic Mesylate $^{18}F^-$ trapping: $^{18}F^-$ (target water, 1.0 ml, 105 MBq) was mixed with water (3 ml) and passed through the column. MeCN (dry, 5 ml) was passed through the column at room temperature followed by MeCN (dry, 5 ml) by syringe pump (flow 30 ml/h, duration 10 min) while heating the column at 60° C. Argon gas was flushed through the column while heating at 60° C. until excess of solvent was removed. The $^{18}F^-$ trapping was 98%.

Radiofluorination: 1-(2-(methylsulfonyl)ethyl)naphthalene (56.0 mg, 224 µmol) was dissolved in toluene (dry, 5 ml) and passed through the column by syringe pump (flow 10 ml/h, duration 30 min) while heating at 90° C. Toluene (dry, 5 ml) was passed through the column by syringe pump (flow 20 ml/h, duration 15 min) while heating at 90° C. to elute the remaining product. The fluorinated product was analyzed by radio-TLC (eluent heptane:EtOAc 80:20). Radiochemical yield was 66% and radiochemical purity was 98%.

Example 2: $^{18}F^-$ Trapping and Radiofluorination of an Aliphatic Tosylate $^{18}F^-$ trapping: $^{18}F^-$ (fraction of target water, 1.0 ml, 311 MBq) was added to the column followed by water (5 ml). MeCN (dry, 5 ml) was passed through the column at room temperature followed by MeCN (dry, 5 ml) by syringe pump (flow 30 ml/h, duration 10 min) while heating the column at 60° C. Argon gas was flushed through the column while heating at 60° C. until excess of solvent was removed. The $^{18}F^-$ trapping was 95%.

Radiofluorination: 1-(2-tosylethyl)naphthalene (68.0 mg, 208 µmol) was dissolved in toluene (dry, 5 ml) and passed through the column by syringe pump (flow 10 ml/h, duration 30 min) while heating at 90° C. Toluene (dry, 5 ml) was passed through the column by syringe pump (flow 20 ml/h, duration 15 min) while heating at 90° C. to elute the remaining product. The fluorinated product was analyzed by radio-TLC (eluent heptane:EtOAc 80:20). Radiochemical yield was 64% and radiochemical purity was 92%.

Example 3: $^{18}F^-$ Trapping and Radiofluorination of an Aliphatic Triflate (Mannose Triflate, FDG Precursor)

$^{18}F^-$ trapping: $^{18}F^-$ (target water, 1.5 ml, 460 MBq) was mixed with water (2 ml) and passed through the column. MeCN (dry, 2 ml) was passed through the column at room temperature followed by MeCN (dry, 8 ml) while heating the column at 60° C. Argon gas was flushed through the column while heating at 60° C. until excess of solvent was removed. The $^{18}F^-$ trapping was 84%.

Radiofluorination: Mannose triflate (50 mg, 100 µmol) was dissolved in toluene (dry, 4 ml) and passed through the column by syringe pump (flow 8 ml/h, duration 30 min) while heating at 90° C. Toluene (dry, 2 ml) was passed through the column by syringe pump (flow 10 ml/h, duration 12 min) while heating at 90° C. to elute the remaining product. The fluorinated product was analyzed by radio-TLC (eluent benzene:MeCN 2:1). Radiochemical yield was 25% and radiochemical purity of acetylated $^{18}F$ FDG was 76%.

Example 4: $^{18}F^-$ Trapping and Radiofluorination of a Nitrated Aromatic Compound $^{18}F^-$ trapping: $^{18}F^-$ (target water, 0.5 ml, 201 MBq) was added to the column followed by water (5 ml). MeCN (dry, 5 ml) was passed through the column at room temperature followed by MeCN (dry, 5 ml) by syringe pump (flow 30 ml/h, duration 10 min) while heating the column at 60° C. Argon gas was flushed through the column while heating at 60° C. until excess of solvent was removed. The $^{18}F^-$ trapping was 98%.

Radiofluorination: 3-methoxy-2-nitropyridine (63.0 mg, 408 µmol) was dissolved in toluene (dry, 5 ml) and passed through the column by syringe pump (flow 10 ml/h, duration 30 min) while heating at 90° C. Toluene (dry, 5 ml) was passed through the column by syringe pump (flow 20 ml/h, duration 15 min) while heating at 90° C. to elute the remaining product. The fluorinated product was analyzed by radio-TLC (eluent petroleum ether:EtOAc 3:1). Radiochemical yield was 14% and radiochemical purity was 45%.

Example 5: $^{18}F^-$ Trapping and Radiofluorination of a Lipophilic Aliphatic Mesylate $^{18}F^-$ trapping: $^{18}F^-$ (target water, 1.2 ml, 752 MBq) was mixed with water (5 ml) and passed through the column using a syringe pump (flow 20 ml/h, duration 9 min). MeCN (dry, 5 ml) was passed through the column at room temperature followed by another portion of MeCN (dry, 5 ml) by syringe pump (flow 30 ml/h, duration 10 min) while heating the column at 60° C. Argon gas was flushed through the column while heating at 60° C. until excess of solvent was removed. The $^{18}F^-$ trapping was 92%.

Radiofluorination: 2,3-bis(hexadecyloxy)propyl methanesulfonate (MsDHG, 63 mg, 101 µmol) was dissolved in toluene (dry, 5 ml) and passed through the column by syringe pump (flow 10 ml/h, duration 30 min) while heating at 90° C. Toluene (dry, 5 ml) was passed through the column by syringe pump (flow 20 ml/h, duration 15 min) while heating at 90° C. to elute the remaining product. The fluorinated product was analyzed by radio-TLC (eluent heptane:EtOAc 95:5). Radiochemical yield was 1% and radiochemical purity was 5%.

Example 6: $^{18}F^-$ Trapping and Radiofluorination of an Aliphatic Bromide $^{18}F^-$ trapping: $^{18}F^-$ (target water, 0.5 ml, 721 MBq) was mixed with water (4.5 ml) and passed through the column at room temperature by syringe pump (flow 20 ml/h, duration 15 min). MeCN (dry, 5 ml) was passed through the column at 60° C. followed by another portion of MeCN (dry, 5 ml) by syringe pump (flow 20 ml/h, duration 15 min) while heating the column at 60° C. Argon gas was flushed through the column while heating at 60° C. until excess of solvent was removed. The $^{18}F^-$ trapping was 94%.

Radiofluorination: NpEtBr (47.73 mg, 203 µmol) was dissolved in toluene (dry, 5 ml) and passed through the column by syringe pump (flow 10 ml/h, duration 30 min) while heating at 90° C. Toluene (dry, 2 ml) was passed through the column by syringe pump (flow 20 ml/h, duration 6 min) while heating at 90° C. to elute the remaining product. The fluorinated product was analyzed by radio-TLC (eluent heptane:EtOAc 80:20). Radiochemical yield was 16% and radiochemical purity was 61%.

Example 7: Investigation of Polymer Supported Bases in On-Column $^{18}F^-$ Trapping and Radiofluorination General Procedure:

A borosilicate glass tube (OD 0.6 mm, length 12 cm) was packed with the polymer-supported base (100 μmol base) mixed with glass beads (212-300 μm, 100-500 mg) and placed in a column oven in a LabView controlled automation apparatus.

$^{18}F^-$ trapping: $^{18}F^-$ (target water, 3.5 mL, 500-5000 MBq) passed through the column at room temperature (flow 1.5 mL/min). MeCN (dry, 4 ml, flow 2 mL/min) was passed through the column at room temperature followed by a helium gas flush through the column until excess of solvent was removed.

Radiofluorination: Toluene (dry, 4 mL, flow 2 mL/min) was passed through the column at room temperature followed by 1-naphthaleneethyl methanesulfonate (100 μmol, 25.03 mg) dissolved in toluene (dry, 3 mL) and passed through the column at 120° C. (flow 0.55 mL/min). Toluene (dry, 2 mL, flow 0.55 mL/min) was then passed through the column to elute the remaining product. The fluorinated product was analyzed by radio-TLC (eluent heptane:EtOAc 80:20)

Synthesis of Polymer Supported Bases:

Polymer-supported $P_2^{tBu}$ (1.6 mmol/g loading), BEMP (2.3 mmol/g loading) and diisopropylaminomethyl (3 mmol/g loading) were obtained from Sigma Aldrich. Amine-functionalized glass beads (30-50 micron, loading unknown) were obtained from Polysciences Europe GmbH. Benzylamine-functionalized polystyrene (0.8-1.2 mmol/g loading), and Merrifield resin (0.8-1.4 mmol/g) were purchased from Bachem. The amine-functionalized polystyrene resin with polyethylene glycol (PEG, 1500-2000 Da) spacer (TentaGel HL, particle size 160 μm, 0.4 mmol/g loading) was obtained from Rapp Polymere.

The amine-functionalized resins/glass beads were reacted with $P_2^{Cl}*BF_4$ (1-chloro-1,1,3,3,3-pentakis(dimethylamino)-1$\lambda^5$-diphosphazen-3-ium tetrafluoroborate) by mixing the support (200-1000 mg) with $P_2^{Cl}*BF_4$ (3 eq to amine) and $Et_3N$ (dry, 9 eq to amine) in DCM (dry, 5 mL) in a glass vial, which was sealed under vacuum. The reaction mixture was then heated with slight agitation at 90° C. for up to three days. This coupling procedure was repeated up to two times in order to ensure good coupling. The resulting resin was deprotonated by reacting the resin with a mixture of KOMe (1 eq to amine) in MeOH (dry, 5 mL) for one hour at room temperature in order to give the desired solid-supported phosphazene base.

Alkylation of the Merrifield resin was done by mixing Merrifield resin with $P_2^{Et}$ (4 eq to chloride) in THF and shaking at room temperature for five days.

TABLE 1

| | Structure | Name | Chemical class | On-column $^{18}F^-$ trapping | On-column radio-fluorination |
|---|---|---|---|---|---|
| 1 | | Diisopropyl-aminomethyl-benzene supported on polystyrene | Non-ionic strong organic base | 0% | 0% |
| 2 | | P-BEMP (2-'Butylamino-2-diethyl-amino-1,3-dimethyl-perhydro-1,3,2-diaza-phosphorine on polystyrene | Non-ionic phosphazene supported on propylene-diamine modified polystyrene | 0% | 0% |
| 3 | | $P_{PS}$-$P_2^{Bz}$ (from benzylamine-functionalized polystyrene) | Non-ionic phosphazene supported on polystyrene | 50% | 0% |

TABLE 1-continued

| | Structure | Name | Chemical class | On-column $^{18}F^-$ trapping | On-column radio-fluorination |
|---|---|---|---|---|---|
| 4 |  | G-P$_2^{Bz}$ (from amine-functionalized glass beads) | Non-ionic phosphazene supported on glass beads | 0% | 0% |
| 5 |  | P$_{PS}$-P$_2^{Et+}$Cl$^-$ (from Merrifield resin) | Ionic phosphazene supported on polystyrene | 99% | Trace |
| 6 |  | P$_{PS}$-P$_2^{tBu}$ (Aldrich resin) | Non-ionic phosphazene supported on polystyrene | 99% | Good |

TABLE 1-continued

| | Structure | Name | Chemical class | On-column $^{18}F^-$ trapping | On-column radio-fluorination |
|---|---|---|---|---|---|
| 7 | | $P_{PS\text{-}PEG}\text{-}P_2^{Bz}$ (from PEG-coated polystyrene) | Non-ionic phosphazene supported on polystyrene | 99% | Good |

Example 8: Investigation of Radiofluorination of Different Substrates Using Polystyrene-Supported $P_2^{tBu}$ General Procedure:

A borosilicate glass tube (OD 0.6 mm, length 12 cm) was packed with PS-supported $P_2^{tBu}$ (150 µmol base, loading 1.6 mmol/g, 93.75 mg) mixed with glass beads (212-300 µm, 100-500 mg) and placed in a column oven in a LabView controlled automation apparatus.

$^{18}F^-$ trapping: $^{18}F^-$ (target water, 3.5 mL, 500-5000 MBq) passed through the column at room temperature (flow 1.5 mL/min). MeCN (dry, 4 ml, flow 2 mL/min) was passed through the column at room temperature followed by a helium gas flush through the column until excess of solvent was removed.

Radiofluorination: Radiofluorination solvent (MeCN for mannose triflate, MeCN/tBuOH 1:5 for FLT-ONs, toluene for the naphthalene analogues and 2-nitro-3-methoxypyridine, dry, 4 mL, flow 2 mL/min) was passed through the column at room temperature followed by the substrate (50-100 µmol) dissolved in radiofluorination solvent (dry, 3 mL) and passed through the column at 120° C. (flow 0.55 mL/min). Radiofluorination solvent (dry, 2 mL, flow 0.55 mL/min) was then passed through the column to elute the remaining product. The fluorinated product was analyzed by radio-TLC (eluent heptane:EtOAc 80:20 for the naphthalene analogues, MeCN:H$_2$O 95:5 for hydrolyzed FDG, DCM:MeOH 9:1 for hydrolyzed FLT, petroleum ether:EtOAc for the pyridine analogue).

TABLE 2

| Entry | Substrate | Product | Radiochemical Yield (%) |
|---|---|---|---|
| 1 | Mannose triflate | $^{18}F$ FDG | 40 |
| 2 | FLT-ONs | $^{18}F$ FLT | 7 |
| 3 | Naphthylethyl mesylate | $^{18}F$ NpEtF | 51 |
| 4 | Naphthylethyl tosylate | $^{18}F$ NpEtF | 34 |
| 5 | Naphthylethyl chloride | $^{18}F$ NpEtF | 16 |
| 6 | Naphthylethyl bromide | $^{18}F$ NpEtF | 42 |
| 7 | Naphthylethyl iodide | $^{18}F$ NpEtF | 18 |
| 8 | 2-nitro-3-methoxypyridine | $^{18}F$ 2-fluoro-3-methoxypyridine | 23 |

Example 9: Investigation of Radiofluorination of Different Substrates Using $P_{PS\text{-}PEG}\text{-}P_2^{Bz}$ General Procedure:

A borosilicate glass tube (OD 0.6 mm, length 12 cm) was packed with $P_{PS\text{-}PEG}\text{-}P_2^{Bz}$ (150 µmol base, loading 0.4 mmol/g, 375 mg) and placed in a column oven in a LabView controlled automation apparatus.

$^{18}F^-$ trapping: $^{18}F^-$ (target water, 3.5 mL, 500-5000 MBq) passed through the column at room temperature (flow 1.5 mL/min). MeCN (dry, 2 ml, flow 2 mL/min) was passed through the column at room temperature followed by MeCN (dry, 2 ml, flow 2 mL/min) at 50° C.

Radiofluorination: Radiofluorination solvent (MeCN for mannose triflate, toluene for FLT-ONs, the naphthalene analogues and 2-nitro-3-methoxypyridine, dry, 4 mL, flow 2 mL/min) was passed through the column at 50° C. followed by the substrate (50-100 µmol) dissolved in radiofluorination solvent (dry, 3 mL) and passed through the column at 120° C. (85° C. for mannose triflate, flow 0.55 mL/min). Radiofluorination solvent (dry, 2 mL, flow 0.55 mL/min) was then passed through the column to elute the remaining product. The fluorinated product was analyzed by radio-TLC (eluent heptane:EtOAc 80:20 for the naphthalene analogues, benzene:MeCN 2:1 for unhydrolyzed FDG, EtOH:EtOAc 1:1 for unhydrolyzed FLT, petroleum ether:EtOAc for the pyridine analogue)

TABLE 3

| Entry | Substrate | Product | Radiochemical Yield (%) |
|---|---|---|---|
| 1 | Mannose triflate | 18F FDG | 36 |
| 2 | FLT-ONs | 18F FLT | 5 |
| 3 | Naphthylethyl mesylate | 18F NpEtF | 38 |
| 4 | Naphthylethyl tosylate | 18F NpEtF | 24 |
| 5 | Naphthylethyl chloride | 18F NpEtF | Trace |
| 6 | Naphthylethyl bromide | 18F NpEtF | Trace |
| 7 | Naphthylethyl iodide | 18F NpEtF | Trace |
| 8 | 2-nitro-3-methoxypyridine | 18F 2-fluoro-3-methoxypyridine | Trace |

Example 10: Investigation of Reusability of the Polystyrene-Supported P$_2^{tBu}$ Radiofluorination Approach General Procedure:

A borosilicate glass tube (OD 0.6 mm, length 12 cm) was packed with PS-supported P$_2^{tBu}$ (100-140 μmol base, loading 1.6 mmol/g) mixed with glass beads (212-300 μm, 100-500 mg) and placed in a column oven in a LabView controlled automation apparatus. Two columns, A and B, were prepared in this manner, and each was used for assessing reusability of the column.

$^{18}$F$^-$ trapping: $^{18}$F$^-$ (target water, 3.5 mL, 500-5000 MBq) passed through the column at room temperature (flow 1.5 mL/min). MeCN (dry, 4 ml, flow 2 mL/min) was passed through the column at room temperature followed by a helium gas flush through the column until excess of solvent was removed.

Radiofluorination: Toluene, dry, 4 mL, flow 2 mL/min) was passed through the column at room temperature followed by the substrate (50 μmol) dissolved in toluene (dry, 3 mL) at 120° C. (flow 0.55 mL/min). Toluene (dry, 2 mL, flow 0.55 mL/min) was then passed through the column to elute the remaining product. The fluorinated product was analyzed by radio-TLC (eluent heptane:EtOAc 80:20).

These procedures were repeated up to two times.

TABLE 4

| Exp. No. | Column | P—P$_2^{tBu}$ μmol | Trapping % | RCP % | RCY % |
|---|---|---|---|---|---|
| First use | A | 140 | 100 | 74 | 43 |
| Second use | A | 140 | 100 | 94 | 69 |
| Third use | A | 140 | 100 | 92 | 61 |
| First use | B | 100 | 98 | 80 | 46 |
| Second use | B | 100 | 100 | 89 | 62 |
| Third use | B | 100 | 100 | 93 | 64 |

The invention claimed is:

1. A method of conducting radiofluorination of a substrate, comprising the steps of:

(a) contacting an aqueous solution of [$^{18}$F] fluoride with a polymer supported phosphazene base selected from R = alkyl and wherein the PEG (polyethylene glycol) has a molecular weight in the range 1500-2000 Da and wherein is polystyrene, for sufficient time for trapping of [$^{18}$F] fluoride on the polymer supported phosphazene base; and (b) contacting a solution of the substrate with the polymer supported phosphazene base having [$^{18}$F] fluoride trapped thereon obtained in step (a) for sufficient time for a radiofluorination reaction to take place.

2. The method according to claim 1, wherein the substrate used in step (b) is an aliphatic or aromatic compound comprising a leaving group.

3. The method according to claim 2, wherein the leaving group is selected from the group consisting of triflate, nosylate, mesylate, tosylate, chloride, bromide, iodide and nitro.

4. The method according to claim 2, wherein the compound comprising the leaving group is selected from naphthylethyl compounds, mannose, optionally substituted pyridine compounds and glycols.

5. The method according to claim 1, wherein the polymer supported phosphazene base is contained in a column.

6. The method according to claim 1, wherein the polymer supported phosphazene base is of the general formula R = alkyl and R is selected from the group consisting of methyl, ethyl, propyl, butyl, isopropyl, isobutyl, tert-butyl, pentyl, isopentyl, tert-pentyl, and tert-octyl.

7. The method according to claim 6, wherein R is selected from the group consisting of ethyl, tert-butyl and tert-octyl.

8. The method according to claim 1, wherein the polymer supported phosphazene base is selected from and

9. The method according to claim 1, wherein step (b) comprises heating the polymer supported phosphazene base having [$^{18}$F] fluoride trapped thereon in contact with the substrate solution to a temperature of from 50° C. to 120° C.

10. A method of preparation of a radiotracer for administration to a patient, comprising the radiofluorination method according to claim 1, followed by a step of formulation of the product of step (b) for administration to the patient.

11. An apparatus for conducting radiofluorination reactions, comprising a polymer supported phosphazene base selected from a phosphazene of the general formula R = alkyl and a phosphazene of the formula contained in a column.

12. The apparatus of claim 11, wherein R is selected from the group consisting of methyl, ethyl, propyl, butyl, isopropyl, isobutyl, tert-butyl, pentyl, isopentyl, tert-pentyl, and tert-octyl.

13. The apparatus of claim 12, wherein R is selected from the group consisting of ethyl, tert-butyl and tert-octyl.

14. The apparatus of claim 11, wherein the polymer supported phosphazene base is selected from and 15. An apparatus for production of a dose of a radiotracer for administration to a patient, which apparatus comprises:
(a) a cyclotron;
(b) a radiosynthesis module, comprising an apparatus according to claim 11; and
(c) a formulation module.

16. The apparatus of claim 15, wherein the radiosynthesis module further comprises one or more of: a heating element, a gas supply, and a second column containing solid phase adsorbent.

* * * * *